(12) United States Patent
Rajwa et al.

(10) Patent No.: US 8,831,889 B2
(45) Date of Patent: Sep. 9, 2014

(54) QUANTIFICATION OF DIFFERENCES BETWEEN MEASURED VALUES AND STATISTICAL VALIDATION BASED ON THE DIFFERENCES

(75) Inventors: Bartlomiej P. Rajwa, West Lafayette, IN (US); Tytus S. Bernas, Dundrum (IE); Joseph P. Robinson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 678 days.

(21) Appl. No.: 12/935,366

(22) PCT Filed: Mar. 31, 2009

(86) PCT No.: PCT/US2009/038995
§ 371 (c)(1),
(2), (4) Date: Sep. 29, 2010

(87) PCT Pub. No.: WO2009/146036
PCT Pub. Date: Dec. 3, 2009

(65) Prior Publication Data
US 2011/0066385 A1    Mar. 17, 2011

Related U.S. Application Data

(60) Provisional application No. 61/041,562, filed on Apr. 1, 2008.

(51) Int. Cl.
| | |
|---|---|
| *G01N 33/48* | (2006.01) |
| *G01N 33/50* | (2006.01) |
| *G01N 31/00* | (2006.01) |
| *G06F 19/12* | (2011.01) |
| *G06F 19/24* | (2011.01) |
| *G06F 17/16* | (2006.01) |
| *G06F 17/10* | (2006.01) |
| *G06F 17/11* | (2006.01) |

(52) U.S. Cl.
CPC ............... *G06F 19/12* (2013.01); *G06F 19/24* (2013.01); *G06F 17/16* (2013.01); *G06F 17/10* (2013.01); *G06F 17/11* (2013.01)
USPC ................... 702/19; 702/22; 702/27

(58) Field of Classification Search
None
See application file for complete search history.

(56) References Cited

U.S. PATENT DOCUMENTS 5,380,663 A * 1/1995 Schwartz et al. ............... 436/10

OTHER PUBLICATIONS

Han et al. Quantum-dot-tagged microbeads for multiplexed optical coding of biomolecules. Nature Biotechnology, 2001, vol. 19, pp. 631-635.*

Roederer et al. Probability binning comparison: A metric for quantitating univariate distribution differences. Cytometry, 2001, vol. 45, pp. 37-46.*
Schwartz et al. Journal of Research of the National Institute of Standards and Technology, vol. 107, 2002, pp. 83-91.*
Wang et al. Journal of Research of the National Institute of Standards and Technology, vol. 107, 2002, pp. 339-353.*
Gaigalas et al. Journal of Research of the National Institute of Standards and Technology, vol. 106, 2001, pp. 381-389.*
Faloutsos et al. Efficient and effective querying by image content. Journal of Intelligent Information Systems, 1994, vol. 3, pp. 231-262.*
Seidl et al. Efficient user-adaptable similarity search in large multimedia databases. Proceedings of the 23rd VLDB Conference, 1997, pp. 506-515.*
Larson et al. Calculus with Analytic Geometry: Alternate Fourth Edition. Lexington, Massachusetts: D. C. Heath and Company, 1990, p. 732.*
Bernas, Tytus, et al., "Quadratic form: a robust metric for quantitative comparison of flow cytometric histograms," 73A(8) *Cytometry Part A* 715-726 (Jun. 16, 2008).
Comeau, Jonathan W., et al., "A guide to accurate fluorescence microscopy colocalization measurements," 91(12) *Biophysical Journal* 4611-4622 (Dec. 2006).
Costantino, Santiago, et al., "Accuracy and Dynamic range of spatial image correlation and cross-correlation spectroscopy," 89(2) *Biophysical Journal* 1251-1260 (Aug. 2005).
Costantino, Santiago, et al., "Semi-automated quantification of filpodial dynamics," 171(1) *Journal of Neuroscience Methods* 165-173 (Feb. 26, 2008).
Dorn, Jonas F., et al., "Computational processing and analysis of dynamic fluorescence image data," 85 *Methods in Cell Biology* 497-538 (Dec. 22, 2007).
Kudryavtsev, Volodymyr, et al., "Monitoring dynamic systems with multiparameter fluorescence imaging," 387(1) *Analytical and Bioanalytical Chemistry* 71-82 (Dec. 2, 2006).
Written Opinion of the International Search Authority and International Search Report for International Application No. PCT/US2009/038995, dated Nov. 17, 2009 (6 pages).

* cited by examiner

*Primary Examiner* — Russell S Negin
(74) *Attorney, Agent, or Firm* — Brinks Gilson & Lione

(57) ABSTRACT

A system and method of validating differences between measured values of fluorescence intensities obtained from a fluorescence-based instrument, including: generating calibration histograms for calibration beads run through the instrument; calibrating a distance function configured to measure distances between the histograms by: constructing a metric using the distance function, which includes a bin-to-bin dissimilarity matrix; and populating the dissimilarity matrix to maximize the following conditions: (A) the distance function of two histograms representing two sets of different beads equals the difference of their MESF values; and (B) the distance function of two histograms representing fluorescence of two sets of identical beads is zero; applying the metric to flow cytometry histograms generated for biological samples, to determine distances between the histograms; constructing a statistical test using the metric to determine a statistical significance of the distances; and determining whether the histogram results from the biological samples are reliable based on the statistical significance.

24 Claims, 4 Drawing Sheets

QUANTIFICATION OF DIFFERENCES BETWEEN MEASURED VALUES AND STATISTICAL VALIDATION BASED ON THE DIFFERENCES

REFERENCE TO EARLIER FILED APPLICATIONS

This application is a 371 national phase of PCT/US2009/038995, filed Mar. 31, 2009, and claims the benefit under 35 U.S.C. §119(e) of U.S. Provisional Application No. 61/041,562, filed Apr. 1, 2008, the disclosures of which are incorporated, in their entirety, by this reference.

BACKGROUND

The present application relates to a system and methods for quantifying differences in measured values within histograms, and more specifically, for automation of calibration of a flow cytometer (or other fluorescence-based instrument) based on construction and use of a distance function having a bin-to-bin dissimilarity matrix, to determine a statistical significance of distance between histograms, and reproducibility of measurements performed on flow cytometry systems.

Flow cytometry is a general technique for counting, examining, and sorting large numbers of microscopic particles suspended in a stream of fluid. It allows simultaneous multiparametric analysis of the physical and/or chemical characteristics of single particles flowing through an optical and electronic detection apparatus using light scattering, fluorescence, and absorbance measurements.

Modern flow cytometers are able to analyze several thousand particles every second, in "real time," and can actively separate and isolate particles having specified properties. A flow cytometer is similar to a microscope, except that instead of producing an image of the cell, flow cytometry offers "high-throughput" (for a large number of cells) automated quantification of singular values of light scattering, fluorescence or absorbance (integrated over particle volume).

FIG. 1 is a flow diagram of a simplified, conventional flow cytometer 10. The flow cytometer 10 includes a laser 14, a flow cell 16, an optical system including a collection lens 20, a beam splitter 24, a dichroic mirror 28, and a number of optical filters 32. A dichroic mirror is used to reflect light selectively according to a specific wavelength. Accordingly, multiple dichroic mirrors 28 may be used to attempt to direct light of a specific wavelength. The flow cytometer 10 further includes detectors, including a forward-scatter detector 36, a side-scatter detector 40, one or more fluorescence detectors 44, and an absorbance detector (not shown). The absorbance detector, if included, would be aligned in line with the laser beam and would detect loss in axial light, indicating an absorbance thereof. An amplification system (not shown) may also be employed, wherein amplifiers are placed after the detectors to strengthen signals of detected scattered light or fluorescence.

The laser 14 emits excitation light, which is directed onto the flow cell 16, which includes a hydro-dynamically focused stream of fluid having the sample of interest. More specifically, the flow cell is a glass, quartz or a plastic piece of fluidic equipment enclosing a stream of sheath fluid, which carries particles. The point of focus of the laser beam within the flow cell 16 is referred to as the interrogation point. The excitation light can come from another source besides a laser. The light scattering and/or fluorescence emission occurs upon illumination (irradiation) of the excitation light, which then passes through the optical system components listed above, depending on the wavelength corresponding to the individual photons that have been excited and their direction of travel.

The detectors listed above are aimed at the point where the fluid stream passes through the light beam; one in line with the light beam (Forward Scatter or FSC) 36, several perpendicular to it (Side Scatter (SSC) 40, and one or more fluorescence detectors 44). Each suspended particle (from 0.2 to 150 micrometers in diameter) passing through the beam scatters the light in some way, and fluorescent chemicals found in the particle or attached to the particle may be excited into emitting luminescence (fluorescence, phosphorescence) or Raman signal. This combination of scattered (or transmitted) and fluorescent light is picked up by the detectors, wherein the scattered light is detected by the forward and side scatter detectors 36, 40 and the emitted light is detected by the fluorescence detectors 44.

The detectors are connected to a computer (FIG. 2), which analyzes the intensity of the light incident at each detector. By analyzing intensities of collected signals at each detector, it is then possible to derive various types of information about the physical and chemical structure of each individual particle of the fluid sample. For instance, FSC correlates with the cell volume and SSC depends on the inner complexity of the particle (i.e. shape of the nucleus, the amount and type of cytoplasmic granules or the membrane roughness).

In summary, and further to different embodiments, a flow cytometer has five main components: (1) the flow cell: includes liquid stream (sheath fluid) to carry and align the particles so that they pass single file through the light beam for sensing; (2) the optical system having illumination sources: lamps (mercury, xenon); high power water-cooled lasers (argon, krypton, dye laser); low power air-cooled lasers (argon (488 nm), red-HeNe (633 nm), green-HeNe, HeCd (UV)); diode lasers (blue, green, red, violet) resulting in light signals; (3) the detectors (typically photomultipliers or avalanche photodiodes) and an Analog-to-Digital Conversion (ADC) system: converting FSC and SSC as well as fluorescence signals from light into electrical signals that can be processed by a computer; (4) the amplification system: linear or logarithmic; and (5) the computer for analysis of the signals. Early flow cytometers were generally experimental devices, but recent technological advances have created a considerable market for the instrumentation, as well as the reagents used in analysis, such as fluorescently-labeled antibodies, calibration beads, and analysis software.

Flow cytometric assays have been developed to determine both cellular characteristics such as size, membrane potential, and intracellular pH, and the levels of cellular components such as DNA, protein, and surface receptors. Measurements in flow cytometry are presented for further interpretation and analysis as distributions of parameters measured in population of cells.

Flow cytometers must be calibrated prior to quantitative fluorescence intensity measurements because variability and drift in detectors, as well as variability of the environment (e.g., changes in ambient temperature). To account for this possible variability, a well-known and well-characterized set of bioparticles is usually analyzed using the cytometry instrument prior to actual experiments. Well-defined characteristics include size, and thus light scatter properties, as well as fluorescence properties. One example of bioparticles that could be used for calibration includes fixed chicken red blood cells. Subsequently, the photomultiplier tube (PMT) voltages of the cytometer are adjusted accordingly to place the peak fluorescence distribution representing the standard into predetermined bins of cytometry histograms. Cells can be substituted by standardized calibration beads, which carry fluorescent labels bound on the surface (e.g., fluorescein, PE, etc). In either case, all the data collected after this calibration process are reported as values relative to the intensity of the standard sample.

The calibration procedure can be further enhanced by use of molecules of equivalent soluble fluorophore (MESF)-calibrated beads. The MESF value of a bead corresponds to the number of fluorescent molecules in solution which give equal fluorescence to that of the bead, to which the same molecules are bound. MESF calibration can be used in flow cytometry as well as in other fluorescence-based methods, such as microarray readers. The assignments of MESF values to a set of labeled beads with different fluorophore densities allow for construction of a calibration curve for an instrument. The procedure allows one to obtain MESF values of biological cells stained with the same fluorescent tag (e.g., fluorophore-labeled monoclonal antibodies). However, this calibration does not take under consideration the fact that with lower amounts of fluorescent labels of surface of beads (or cells), uncertainty of measurement increases: the corresponding histogram peak becomes wider. Therefore, despite calibration, a comparison of samples representing low and high fluorescence intensities cannot be performed in a statistically relevant manner. In other words, statistical significance cannot be assigned.

Flow-cytometry calibration beads are manufactured by a dozen different manufacturers. Calibration of a cytometer has to be performed daily while in use to ensure proper results of live samples. In some clinical systems, this calibration is required to be performed more than once per day. This is not only a question of good practices, but an actual requirement.

The whole calibration process is performed manually, such as described in recent literature. See, e.g., Robert A. Hoffman and James C. S. Wood, Characterization of Flow Cytometer Instrument Sensitivity, *Current Protocols in Cytometry*, 1.20.1-1.20.18 (2007) (describing linear regression calculations to be made with the aid of a spreadsheet); Robert A. Hoffman, Standardization, Calibration, and Control in Flow Cytometry, *Current Protocols in Cytometry*, 1.3.1-1.3.21 (2005). Dr. Hoffman in the second reference listed above quotes from the Clinical Laboratory Standards Institute, an international clinical laboratory standards-setting organization, which stated that "[t]here are no standards which can be used to check the accuracy of flow cytometric test results. Hence, verifying reproducibility of instrument performance is an essential element of daily quality assurance for the flow cytometry laboratory. Instrument performance must be monitored under the same conditions as are used to run test samples." Id. The present disclosure is aimed at ameliorating this lack of standards in checking the accuracy and reproducibility of flow cytometric results.

There exist about 10 thousand clinical analyzers, and about 20-30 thousand research machines in the field for testing. Additionally, there are at least five thousand flow cytometry cell sorters that are calibrated also with the manual, bead method. Accordingly, there is a tremendous need to provide a system and methods to, in an automated fashion, validate measured values of a cytometer, or other fluorescence-based measuring instrument, wherein a standard is provided, outside of which variation in measured values render test results unreliable. This would provide a quality control system that would save a significant amount of time in guess work involved when a cytometer operator is faced with larger-than-normal variations in measured values.

DETAILED DESCRIPTION OF THE DRAWINGS AND THE PRESENTLY PREFERRED EMBODIMENTS

The present application relates to a system and methods for quantifying differences between samples containing fluorescent material measured by a flow cytometer, or some other fluorescence-based instrument. The differences are expressed as distances between histograms of fluorescence intensities calculated using a metric that includes a distance function having a bin-to-bin dissimilarity matrix. More specifically, the disclosure provides for statistical validation of the differences based on construction and use of a statistical test that includes the aforementioned metric with a distance function having a bin-to-bin dissimilarity matrix. Herein, the term difference means calibrated quadratic form (QF) distance (or other suitable distance function) used to compare intensity histograms obtained from flow cytometers. The term dissimilarity may also be used in the context of "similarity" where the intent is to indicate ground distance between individual bins in a histogram. The term dissimilarity will be used, however, for consistency.

The present embodiments will now be further described. In the following passages, different aspects of the embodiments are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Figure 1:
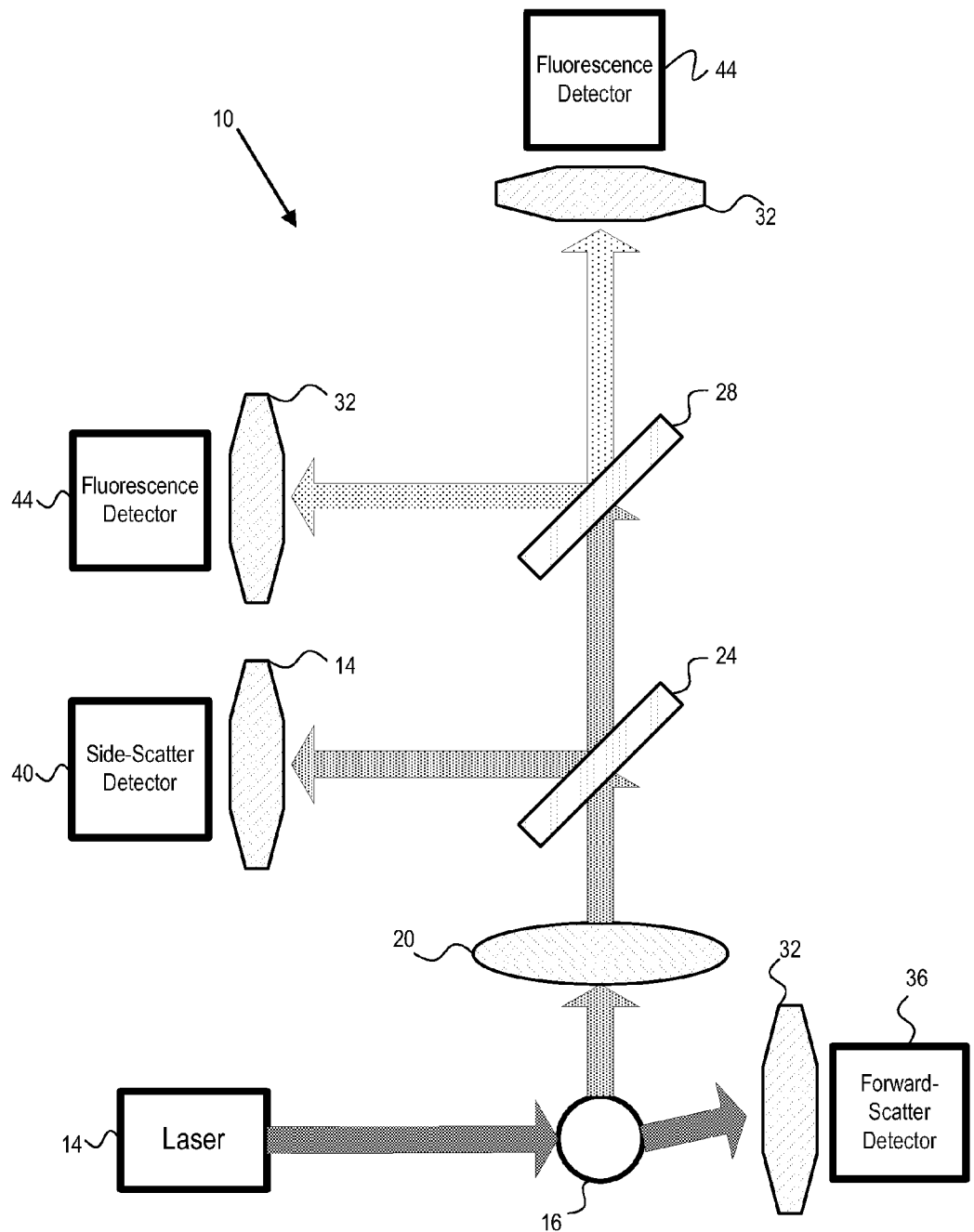
FIG. 1 is a flow diagram of a simplified, conventional flow cytometer.
Figure 2:
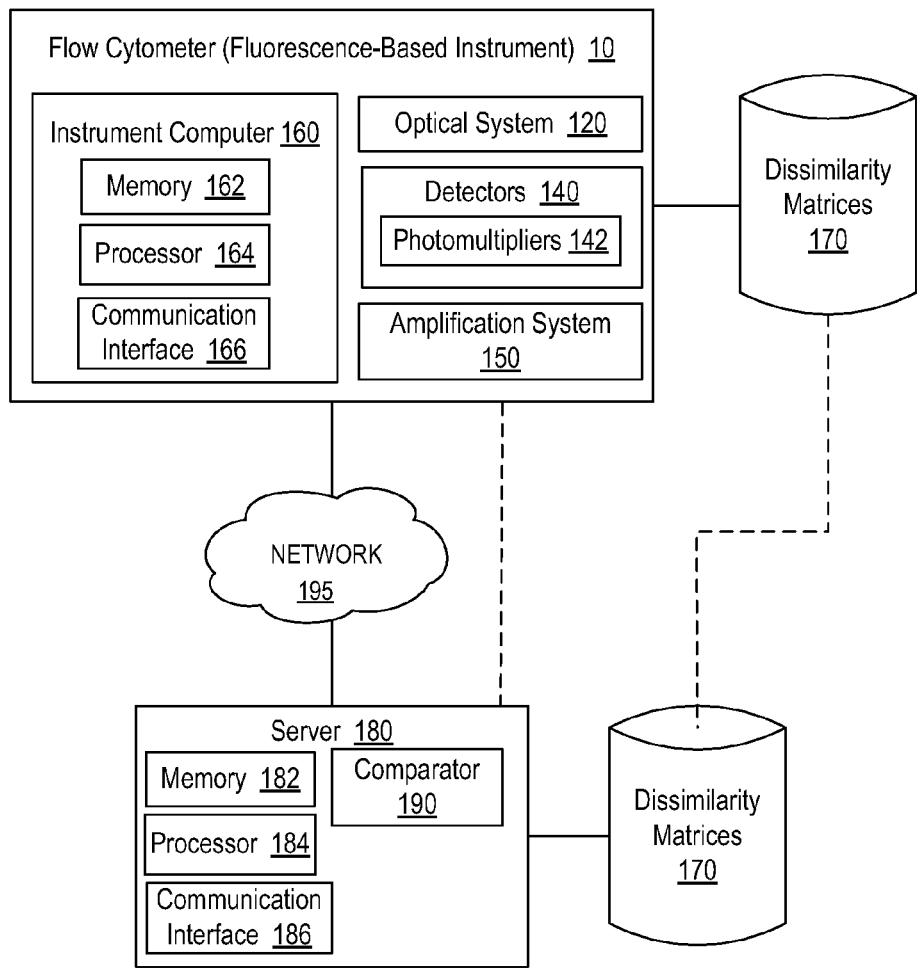
FIG. 2 is a system diagram of a system for quantifying differences between measured values of a cytometer, or other fluorescence-based instrument, and determining a statistical significance of those differences to validate test results.

FIG. 2 is a system diagram of a system 100 for quantifying differences between intensity histograms measured using a cytometer 10, or other fluorescence-based instrument 10, and determining a statistical significance of those differences. As discussed above, the cytometer 10 includes an optical system 120, a plurality of detectors 140, which includes photomultipliers 142 having tubes, and an amplification system 150. These systems interact generally as described with reference to FIG. 1. The cytometer (or instrument) 10 also includes a computer 160 having a memory 162, a processor 164, and a communication interface 166. The cytometer 10 also may include a dissimilarity matrices database 170 coupled therewith. As discussed, the computer 160 is coupled with the detectors 140 to obtain the light scattering and fluorescence information that each respective detector provides. Herein, the phrase "coupled with" is defined to mean directly connected to or indirectly connected through one or more intermediate components. Such intermediate components may include both hardware and software based components.

When running a set of molecules of equivalent soluble fluorophore (MESF)-calibrated beads through the cytometer 10 for calibration, the computer 160 gathers fluorescence intensities, in addition to light scatter intensities, which intensities are represented as a number of counts of detected particles in bins (corresponding to specific intensities) of a histogram. After multiple histograms are stored from test runs of multiple sets of beads, a dissimilarity matrix may then be fitted based on the values of at least two histograms, as described in detail below. The dissimilarity matrices database 170 stores the dissimilarity matrices fitted to the QF metric, for instance, on the basis of known MESF values and intensity histograms measured from sets of calibration beads, or from biological control samples. These various measurements that generate different histograms may result in varying dissimilarity matrices, which may further be compared.

The system 100 also includes a server 180 having a memory 182, a processor 184, a communication interface 186, a comparator 190, and may be coupled with the dissimilarity matrices database 170. The comparator 190 may be coupled with or a part of its processor, and be used to both compare histograms and dissimilarity matrices. The server 180 may include another computing device with sufficient processing power to compute the statistical analysis described below. While these computations and estimates could be calculated by the computer 160 of the instrument 10, many of these instrument computers 160 were not designed to handle such extensive computations. The instrument 10, however, could be retrofitted or manufactured in the future with higher processing capabilities such that the server 180 would not be required. Accordingly, the instrument 10 is coupled with the server 180 and it should be understood that the server 180 could be integrated within the instrument 10.

Furthermore, the server 180 could communicate over a network 195, such as the Internet, the Web, a local area network (LAN), a wide area network (WAN), or other network. The server 180 could be owned by a maintenance company that contracts with laboratories to provide monitoring and repair services, which monitoring could take place over the network 195. As will become apparent, tracking the dissimilarity matrices, and the differences between them over time according to the present disclosure, enables validation of measured values that also usually vary over time. If the dissimilarity matrices belonging to the same instrument 10 vary too much, this could be an indication of potential failure or imminent failure of a component of the instrument 10, requiring a repair trip by the maintenance company. The server 180 and or the instrument computer 160 may monitor these dissimilarity matrices. Of course, such monitoring and maintenance could be performed by testing laboratories, but this may not be fiscally feasible.

As discussed above, there is a tremendous need to provide a system and methods to, in an automated fashion, validate measured values of a cytometer, or other fluorescence-based measuring instrument, wherein a standard is provided, outside of which variation in measured values render test results unreliable. The presented system and methods employ a mathematical metric (and statistic established based upon this metric) for estimation of differences between intensity distributions, such as flow cytometry histograms, reported in calibrated fluorescence units. While various mathematical metrics may be used, the technique disclosed herein may work best with use of quadratic form distance (QF) with a bin-to-bin similarity matrix (A) to construct the metric for this estimation. The QF metric takes on the form of $$QF(h, f) = (h-f)^T A_j^i (h-f) = \sum_{i=1}^{n} \sum_{j=1}^{n} a_{ij}(h_i - f_i)(h_j - f_j), \quad (1)$$

where h and f are vectors that list counts corresponding to each of the cytometry histogram bins (or channels), i, j. These vectors can be normalized so that $0 \leq \{f,h\} \leq 1$ and $\Sigma_i h_i = \Sigma_i f_i = 1$. The i and j are histogram bin numbers in h and f, respectively, and $A_j^i = [a_{ij}]$ is a positive semi-definite matrix of distances between $i^{th}$ and $j^{th}$ bins. In the simplest (linear) case, the elements of the matrix $A_j^i$ may be simply computed as $A_j^i = \sqrt{1+(i-j)^2}$; however, in a more general case, the elements of the matrix may be calculated using the following formula:

$$A_j^i = \exp\left(\gamma \frac{d_{ij}}{d_{max}}\right)^\delta, \quad (2)$$

where $$d_{ij} = |i - j|, \quad d_{max} = \max_{i,j}\{d_{ij}\},$$

or other formula that leads to a positive semi-definite matrix that ensures QF to be a valid metric.

Parameters $\gamma$ and $\delta > 0$ control a global shape of the distance matrix such that the matrix maximizes the two conditions, (1) and (2), discussed below. The higher $\gamma$, the more similar the resulting matrix is to the identity matrix. The QF metric becomes Euclidean for $A_j^i = 1$ (e.g., $a_{ij}=1$ when i=j, otherwise $a_{ij}=0$). Low values of $\gamma$ make the distance matrix more similar to the linear case mentioned before.

To provide an absolute, calibrated measure of differences between fluorescent biological samples, the disclosed technique first employs several sets of MESF-calibrated beads, each characterized by fluorescence intensities corresponding to known numbers of fluorochrome of interest. The MESF beads are run through the flow cytometer (or other instrument) 10 of the flow cytometry system 100, and representative histograms are recorded. After measurement is completed, the next step involves fitting a proper dissimilarity matrix, or matrix of inter-bin distances $A_j^i$, to QF distances between the respective histograms.

The elements of the matrix $A_j^i$ are chosen in order to create a QF metric, which meets at least the following two conditions: (1) the QF value of two histograms representing two sets of different standardized beads substantially equals the difference of their MESF values (or the logarithms of their MESF values); and (2) the QF of two histograms representing fluorescence of two sets of identical MESF beads is substantially zero. By way of further explanation, these conditions attempt to create an appropriate dissimilarity matrix by minimizing QF distances between multiple repeats of calibration samples of one kind (one level of MESF values), and maximizing—or setting as a specific value—distances between samples representing different calibration samples (thus, different MESF values). It therefore follows that at least two intensity levels $\{i_1, i_2\}$, each with at least two histograms $\{h_1, h_2\}$ are required for the procedure of creating the $A_j^i$ matrix. So, for samples with average intensity $i_1$ represented by a set $I_1$ of flow cytometry histograms, and samples with average intensity $i_2$ represented by histograms belonging to set $I_2$, one can generate two sets of pair-wise distances: S (same or similar), and D (different or dissimilar):

$(h_m, h_n) \in S$ if $\{h_m, h_n\} \in I_1 \vee \{h_m, h_n\} \in I_2$ $(h_m, h_n) \in D$ if $(h_m \in I_1 \wedge h_n \in I_2) \vee (h_m \in I_2 \wedge h_n \in I_1)$ Correspondingly, for more than two intensities I:

$(h_m, h_n) \in S$ if $\{h_m, h_n\} \in I_x$ $(h_m, h_n) \in D$ if $(h_m \in I_x \wedge h_n \in I_{x'}) \vee (h_m \in I_{x'} \wedge h_n \in I_x)$,
$\quad x' = \square \backslash \{x\}$ The process of finding the optimal A may be viewed, in part, as minimization of F(A):

$$F(A) = \frac{1}{|S|} \sum_{(h_i, h_j) \in S} QF(h_m, h_n)^2 - \frac{1}{|D|} \sum_{(h_i, h_j) \in D} QF(h_m, h_n)^2 \quad (5)$$

with positive semi-definiteness constraint imposed on $A_j^i$. The first part of the formula, F(A), above describes condition (1), and the second part describes condition (2). The process of finding $A_j^i$ can be realized using a pre-determined function that controls at least groups of elements of the matrix $A_j^i$, such as the formula in Equation 2.

The parameters γ and δ in Equation 2 may be found using a process in order to determine a QF distance that optimally meets the conditions (1) and (2) mentioned above. In other words, the parameters γ and δ are fitted to the function in Equation 2 through iteratively determining values for them until the conditions are as closely met as possible. Because measurement precision in flow cytometry decreases with fluorescence intensity (e.g., MESF number), the dissimilarity between two adjacent bins representing low fluorescence intensities will be proportionally lower than dissimilarity between two bins representing higher fluorescence intensities. Lower fluorescence intensities will correspond to lower indices of the distance matrix $A_j^i$. Consequently, with the appropriate γ and δ, the dissimilarity matrix $A_j^i$ represents measurement precision and resolution of a cytometer at the whole range of fluorescence intensities (MESF values).

For a flow cytometry system using a logarithmic amplifier, an initial guess for an iterative estimation of γ and δ can be obtained by approximating the shape of the dissimilarity matrix in Equation 2 by a function fitted to the below relation:

$$f: \{I_{MESF}^{(1)}, I_{MESF}^{(2)}, \ldots, I_{MESF}^{(n)}\} \to \mathbb{R} \quad (3)$$

$$I_{MESF} \mapsto \mu(I_{MESF}) \exp((\sigma(I_{MESF}))^2 - 1)^{\frac{1}{2}}$$

where $I_{MESF}^{(n)}$ are the known values of fluorescence intensity for every sample of MESF beads used for calibration. The intensity is expressed in MESF units. The term $\sigma(I_{MESF})$ is a standard deviation of the natural logarithm of MESF bead intensities measured in the flow cytometer. The term $\mu(I_{MESF})$ is the mean intensity, which is a geometric mean when histograms are produced by log amplifiers.

By using the above approach, it is assumed that the similarity between two bins in a flow cytometry histogram is not only proportional to their bin-to-bin distance, but is also related to uncertainty of fluorescence intensity measurement. In Equation 3, this uncertainty of measurement is expressed as a coefficient of variance (CV) of a log-normal distribution of the measured calibration beads.

In a second embodiment, an appropriate dissimilarity matrix is built by first approximating the calibrated matrix by using a modification to Equation 2. Instead of employing i and j, one may employ absolute intensity values expressed in MESF. Therefore, histogram bin numbers are substituted by the equivalent MESF values obtained from a smoothed curve showing relation between flow cytometry intensity readout and corresponding MESF values. Accordingly, Equation 2 would take on the form of:

$$A_j^i = \exp\left(\gamma \frac{I_{ij}}{I_{max}}\right)^\delta, \quad (4)$$

where $$I_{i,j} = |I_i - I_j|, \quad I_{max} = \max_{i,j}\{I_{ij}\}.$$

The resolution of fluorescence measurement is determined by the width of the histogram peaks. Wider peaks mean less precise measurement, and narrower peaks mean better distinguishability, and consequently, better resolution. Therefore, the dissimilarity matrix approximated by Equation 4 may be further modified by incorporating the uncertainty of measurement in a form of a weighting function that deemphasizes similarity between the poorly separated intensities while emphasizing the high intensity and low uncertainty measurements:

$$C_i^j = A_i^j \times w, \quad (5)$$

where $$w = \left(\frac{1}{1 + \sqrt{\frac{\sigma_i^2}{I_i^2} + \frac{\sigma_j^2}{I_j^2}}}\right).$$

The dissimilarity matrix $A_j^i$ is thereby modified by w as demonstrated in Equation 5, wherein the weighting function w includes large values for fluorescence intensities that are easy to distinguish and low values for fluorescence intensities that are difficult to distinguish, thereby scaling the distance matrix to include measurement precision.

The resultant dissimilarity matrix ($A_j^i$ in the first embodiment and $C_i^j$ in the second embodiment, both of which may be referred to interchangeably herein) can be stored, and subsequently used to document, monitor and compare changes in instrument accuracy and resolution over time. If a set of experiments requires use of flow cytometer over an extended period of time, calibration using MESF is likely to be repeated. In order to ensure comparability of the results, a calibration process may be repeated as previously described and a new dissimilarity matrix for the QF metric may be computed. The possible changes in the accuracy and resolution of the flow cytometry instrument may be expressed as a difference (e.g., mean squared error, MSE) between $C_i^{j'}$ and $C_i^j$ or between $A_i^{j'}$ and $A_i^j$.

In statistics, bootstrapping is a modern, computer-intensive, general purpose approach to statistical inference, falling within a broader class of resampling methods. Bootstrapping is the practice of estimating properties of an estimator (such as its variance) by measuring those properties when sampling from an approximating distribution. One standard choice for an approximating distribution is the empirical distribution of the observed data, which is the case in this disclosure. In a situation where a set of observations can be assumed to be from an independent and identically-distributed population, this can be implemented by constructing a number of resamples of the observed dataset (and of equal size to the observed dataset), each of which is obtained by random sampling with replacement from the original dataset.

Bootstrapping may also be used for constructing hypothesis tests. It is often used as an alternative to inference based on parametric assumptions when those assumptions are in doubt, or where parametric inference is impossible or requires very complicated formulas for the calculation of standard errors. The advantage of bootstrapping over analytical methods is its great simplicity: it is straightforward to apply the bootstrap to derive estimates of standard errors and confidence intervals for complex estimators of complex parameters of the distribution, such as percentile points, proportions, odds ratio, and correlation coefficients. Bootstrapping may be used in the present application as will become apparent below.

The calibrated QF metric as estimated by the above-described procedures based on the MESF beads, including empirically-constructing the distance matrix, $A_j^i$, characterizes only the instrument to be calibrated, not the larger experimental process. While calibration of the instrument is important so that confidence is maintained in experimental results obtained by use of the instrument, of perhaps greater interest is the variability (or statistical difference) between experimental runs through the instrument when dealing with live, biological samples. Accordingly, the calibrated QF metric may be applied to a biological sample for performing a live test, e.g., to use it as a tool to test for a statistical significance in a difference between experimental control and test samples. To do so, a control sample is used to set a baseline of a set of control parameters and conditions, with a goal of generating empirical significance levels of measured data. The levels are empirical in the sense that they incorporate all the biological variability and the variability present due to sampling error, pipetting problems, and other possible issues involved with sample preparation. The control sample is prepared and run through the instrument, which generates a set of cytometry histograms representing the biological control in the experiment.

Next, the calibrated QF metric may be applied to calculate a set of distances, expressed in MESF, between a set of histograms generated by random sampling, with replacement, (e.g., bootstrapping) the cytometry histograms representing the biological control. The resultant distances may be used to create a distribution of differences. This distribution of differences between bootstrapped histograms demonstrate effects of instrumental variability as well as biological and biochemical variability of labeling procedures (e.g., staining with fluorescent species). Bootstrapping was discussed above, and herein it may be used to help assign significance levels to differences between sampled histograms.

Finally, with the bootstrapped distributions in place, statistical significance levels for the differences between samples in the experiment of interest are established. The simplest approach may involve taking α quantile (bootstrap percentile) of the estimated values. The α quantile of a data set is defined as that value where an α fraction of the data is below that value. Therefore, the measured QF distance between two samples may be considered statistically significant if the distance obtained from the bootstrapped control samples is greater than the observed value for the tested samples in less than a determined percentage of a total number of the bootstrapped calculations, performed n times. The number of times, n, the bootstrapped calculations are made is based on the number of permutations required, with varying sample size, to obtain a reliable estimation of percentiles. The determined percentile may be, for instance, 1% of the time. That is, the null hypothesis is rejected at the 1% statistical significance level, wherein if the control sample bootstrapped values are below the observed value in 0-99% of the test samples, then there is no statistically significant difference. Since the test is constructed on the basis of QF distance, which cannot be negative, the 1% level of significance is the level of significance of one-tailed hypothesis testing. One-tailed hypothesis testing refers to directional hypotheses, wherein deviation from the null value is clearly specified, e.g., a specific predicted outcome is stated.

A calibrated QF metric was applied to estimate the differences between histograms of DNA content (ploidy) in cells of old and young leaf tissue of *Brassica campestris*. Furthermore, differences in fluorescence intensity in immunostaining of human lymphocytes were quantified. Results indicated that the QF distance function provides a true (mathematical) metric for estimation of distance between flow cytometry histograms of arbitrary shape. The QF metric can be applied as a statistical test for estimation of significance of the distance measure, as just discussed above. The respective critical values depend only on the number of events and standard deviations of compared histograms and are not affected by distribution shape. Therefore, applications of the QF do not require assumptions concerning distribution shape, which facilitates practical implementation. This result was confirmed using empirical distributions of DNA content in plant tissue and distributions of immunofluorescence in human cells.

Figure 3:
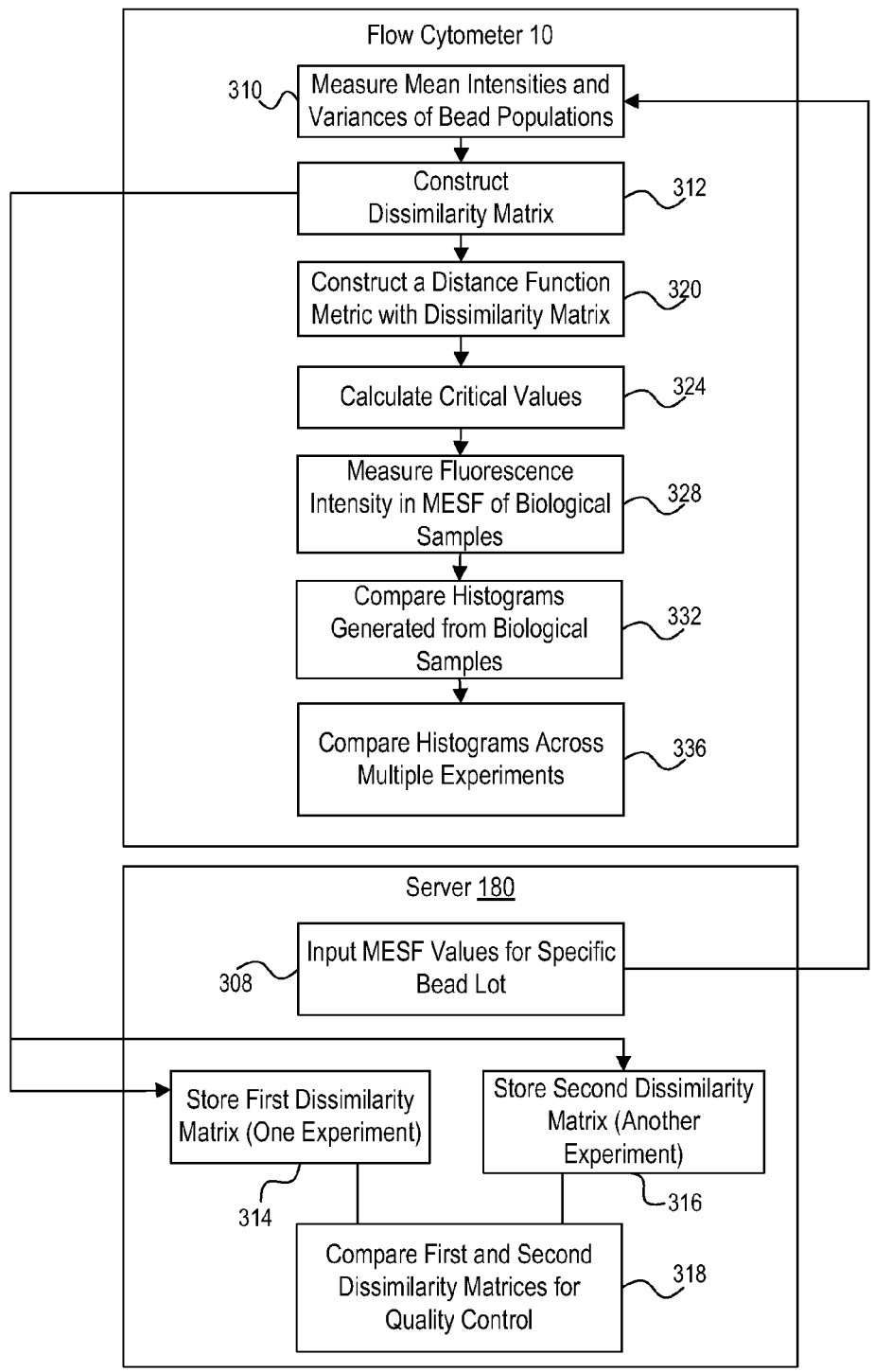
FIG. 3 is a flow chart of a method for quantifying and validating differences between biological samples on the basis of their flow cytometry intensity histograms.

FIG. 3 is a flow chart of a method for quantifying and validating differences between biological samples on the basis of their flow cytometry intensity histograms. At block 308, the server 180 inputs MESF values for a specific lot of beads into the cytometer 10 for calibration beads to be used in the cytometer 10. When the cytometer 10 goes through calibration, the operator enters the batch number into the instrument computer 160, and the server 180 informs the instrument computer about the intensities of bead populations used during calibration which are a part of the lot being used.

At block 310, the cytometer 10 measures the mean intensities and variances of different bead populations, generating histograms for the bead populations. At block 312, the instrument computer 160 constructs a first (bin-to-bin) dissimilarity matrix based on data provided from the instrument 10 when running the beads and the information from the server 180. The first dissimilarity matrix is unique for a given cytometer (or instrument) 10 and, at block 314, is stored in the dissimilarity matrices database 170. The first dissimilarity matrix should not change substantially if the cytometer is stable and well aligned. The process of steps 308 through 314 can be repeated in at least one other experiment with the same bead populations to generate a second dissimilarity matrix, which is stored in the dissimilarity matrices database 170 at block 316. At block 318, the first and second dissimilarity matrices can be compared with each other for the purpose of stability and quality control, enabling continual monitoring of the reliability of the measured values from the cytometer or other instrument 10. If the dissimilarity matrices are significantly different from each other, the computer 160 or the server 180 may warn the operator of a detected instability in the instrument 10 that would render histogram results unreliable. The significance level required to trigger a warning may be set by the operator based on the reliability of performed measurement (assay). Currently, however, there are no established standards with regards to reliability, as discussed in the background section above.

Additionally, measurement metadata such as ambient temperature, detector settings, specific laser used and/or its power level, filters, etc., may also be stored with, or in relation to, each dissimilarity matrix in the dissimilarity matrices database 170. This measurement metadata may be used in the future to establish optimal cytometer settings for a given application of the cytometer 10, essentially aiding in calibration.

Furthermore, steps 320 through 336 (discussed below) could be performed by the server 180 on its stored dissimilarity matrices for the purpose of determining the reliability of current sets of measured values generated by the cytometer 10 when compared with past results. And, of course, the steps 320 through 336 could be executed by the instrument computer 10 to give the operator a real-time indication of the reliability of its results, and the comparator 190 may be available to either the instrument computer 160 or to the server 180 for purposes of making histogram or matrix comparisons. The steps 320 through 336 will, therefore, be explained with reference to the cytometer 10 for sake of simplicity.

At block 320, the instrument computer 160 constructs a metric using the QF (or other) distance function with the first dissimilarity matrix, e.g., the dissimilarity metric generated with use of the calibration beads. The metric is also unique for a given cytometer 10, but with use of the measurement metadata described above, the metric could be used on another cytometer as now described. At block 324, the computer 160 calculates empirical critical values for each set of control samples to be used to verify significance of differences between compared test samples. The critical values may be established by taking a quantile (bootstrap percentile) of the estimated values. The critical values may, therefore, be established as a percentile of distribution of QF distances corresponding to the control sample (or calibration bead) distributions, expressed in histograms, above which the QF distance corresponding to the later-measured biological samples should fall to be considered statistically different. For instance, the computer 160 may generate confidence intervals by bootstrapping the histograms of the control samples, and set each critical value as being within a desired percentile of a corresponding confidence interval of a control sample.

At block 328, the cytometer 10 measures fluorescence intensities in MESF of biological samples, generating a histogram for each sample. Also, at block 328, bootstrapping may be used to generate additional histograms (for use in subsequent statistical analysis) by randomly sampling, with replacement, the dataset. At block 332, the computer 160 compares histograms obtained from the samples, through application of the QF metric, to determine differences between samples and their statistical significance. A critical value could be made a part of the measurement metadata appended to a corresponding dissimilarity matrix as described above, which may allow for comparison of preparation reproducibility, e.g., on the same cytometer 10 at a different time or on a different cytometer 10.

At block 336, the computer 160 may compare histograms across multiple experiments conducted at different times and on different days. This may also include a comparison of dissimilarity matrices discussed with reference to block 318. This is possible because the elements in the matrices correspond to fluorescence intensities in absolute (MESF) values. This comparison is used for quality control as the matrices contain information on the range of intensities measured with the instrument (dynamic range) and precision of such measurement at each intensity level (intensity resolution).

Figure 4:
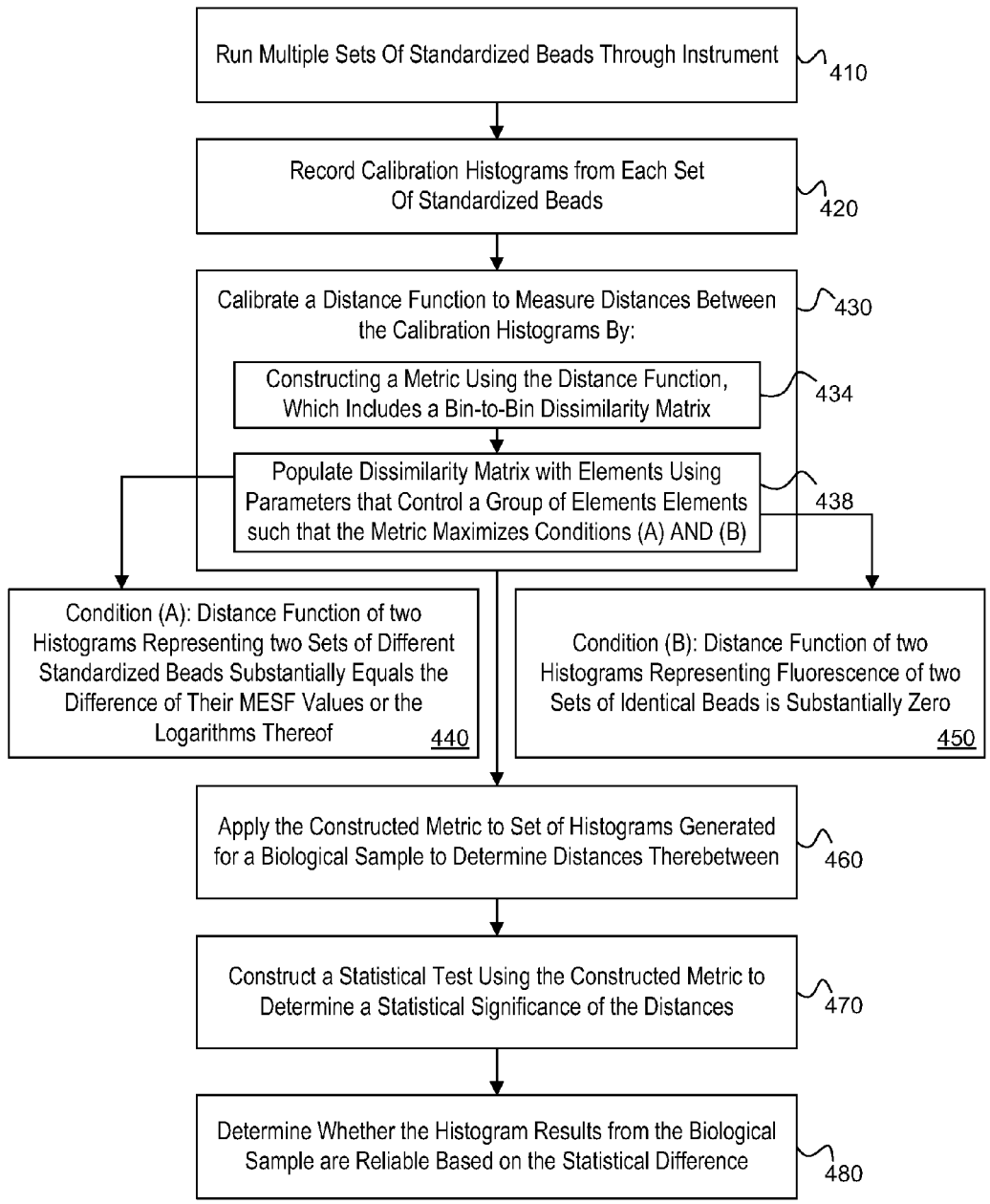
FIG. 4 is a flow chart of another method for quantifying and validating differences between biological samples on the basis of their flow cytometry intensity histograms.

FIG. 4 is a flow chart of another method for quantifying and validating differences between biological samples on the basis of their flow cytometry intensity histograms. At block 410, multiple sets of standardized beads are run through the instrument to generate, at block 420, at least one calibration histogram for each set of beads for the instrument, the histograms containing molecules of equivalent soluble fluorophore (MESF) values. At block 430, a computer coupled with the instrument calibrates a distance function (such as QF) configured to measure distances between the calibration histograms generated by the sets of standardized beads, including, at block 434, constructing a metric using the distance function, which includes a bin-to-bin dissimilarity matrix, and at block 438, populating the dissimilarity matrix with elements using parameters that control at least groups of the elements such that the metric maximizes the below conditions (A) and (B) at substantially the whole range of MESF values for the sets of standardized beads. At block 440, condition (A) is that the distance function of two histograms representing two sets of different standardized beads substantially equals the difference of their MESF values or the logarithms of their MESF values. At block 450, condition (B) is the distance function of two histograms representing fluorescence of two sets of identical beads is substantially zero.

At block 460, the computer applies the constructed metric to a set of flow cytometry histograms generated by the instrument for a plurality of biological samples, to determine distances between the histograms. At block 470, the computer constructs a statistical test using the constructed metric to determine a statistical significance of the distances between the histograms. At block 480, the computer determines whether the histogram results from the biological samples are reliable based on the statistical significance.

The preferred embodiments of the present invention provide numerous advantages, including: 1.) Absolute calibration (signal intensity expressed as a corresponding number of fluorophore molecules) in the whole instrument range, e.g., not only at signal levels corresponding to maxima of bead intensity distribution. 2.) Instrumental noise (precision) taken into account in the calibration, and therefore, the proposed method is more robust than methods used currently. 3.) Differences between histogram distributions corresponding to biological samples (hence of arbitrary shape) may be quantified (expressed in absolute units). 4.) The comparison between histograms is executed using a mathematical metric so any two distributions can be compared, not just the control with a test sample. 5.) The metric can detect changes in distribution shape, e.g., in every distribution moment, not only in some parameters (e.g., mean or variance). 6.) Statistical significance can be assigned to the comparison representing the probability that measured samples are biologically different, whereas instrumental and preparation errors do not affect the result. 7.) Quantitative and statistical comparison of distributions generated using different machines is possible (provided that they are calibrated). Other advantages may be recognizable in the teachings disclosed herein; accordingly, this is an exemplary list of advantages.

The system and process described may be encoded in a signal bearing medium, a computer readable medium such as a memory, programmed within a device such as one or more integrated circuits, one or more processors or processed by a controller or a computer. If the methods are performed by software, the software may reside in a memory resident to or interfaced to a storage device, synchronizer, a communication interface, or non-volatile or volatile memory in communication with a transmitter. A circuit or electronic device may be designed to send data to another location. The memory may include an ordered listing of executable instructions for implementing logical functions. A logical function or any system element described may be implemented through optic circuitry, digital circuitry, through source code, through analog circuitry, through an analog source such as an analog electrical, audio, or video signal or a combination. The software may be embodied in any computer-readable or signal-bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine readable medium," "propagated-signal" medium, and/or "signal-bearing medium" may include any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A method of quantifying and validating differences between measured values of fluorescence intensities obtained using a flow cytometer or other fluorescence-based instrument, the method comprising:
   a) running multiple sets of standardized particles through the instrument to generate at least one calibration histogram for each set of particles, the histograms containing fluorescence intensity values;
   b) calibrating, with a computer coupled with the instrument, a distance function configured to measure distances between the calibration histograms generated by the sets of standardized particles, comprising:
      i) constructing a quadratic form (QF) metric using the distance function, where the QF metric comprises $$QF(h, f) = (h-f)^T A_j^i (h-f) = \sum_{i=a}^{n} \sum_{j=1}^{n} a_{ij}(h_i - f_i)(h_j - f_j),$$

where h and f are histograms, and A comprises a bin-to-bin dissimilarity matrix that is an n×n positive semi-definite matrix, n being the number of bins in histograms h and f; and
      ii) populating entries of the dissimilarity matrix with elements using parameters that control at least groups of the elements such that the metric maximizes the following conditions at substantially the whole range of fluorescence intensity values for the sets of standardized particles: (A) the distance function of two histograms representing two sets of different standardized particles substantially equals the difference of their fluorescence intensity values or the logarithms of their fluorescence intensity values; and (B) the distance function of two histograms representing fluorescence of two sets of identical particles is substantially zero;
      wherein each set of particles is characterized by a fluorescence intensity corresponding to a known number of fluorochromes of interest, wherein the dissimilarity matrix further includes distances between bins i,j of histograms h,j which list counts of detected fluorescence intensities corresponding to each of the cytometry histogram bins;

$$A_j^i = \exp\left(\gamma \frac{d_{ij}}{d_{max}}\right)^\delta,$$

where $$d_{i,j} = |i - j|, d_{max} = \max_{i,j}\{d_{i,j}\};$$

iii) computing and
      iv) iteratively determining $\gamma$ and $\delta$ of $A_j^i$ to control a global shape of the dissimilarity matrix such that maximizes the conditions of b)ii)A) and b)ii)B);
   c) applying, by the computer, the constructed metric to a set of flow cytometry histograms generated by the instrument for a plurality of biological samples, to determine distances between the histograms;
   d) constructing and applying a statistical test, by the computer, using the constructed metric to determine a statistical significance of the distances between the histograms; and
   e) determining, by the computer, whether the histogram results from the biological samples are reliable based on the statistical significance.

2. The method of claim 1, further comprising:
   normalizing the histograms h and f so that $0 \le \{f,h\} \le 1$ and $\Sigma_i h_i = \Sigma_i f_i = 1$.

3. The method of claim 1, wherein the standardized particles comprise standardized beads, and wherein the fluorescence intensity is expressed in molecules of equivalent soluble fluorophore (MESF), the method further comprising:
   initially estimating $\gamma$ and $\delta$ by approximating the shape of the dissimilarity matrix by a function fitted to the following relation:

$$f: \{I_{MESF}^{(1)}, I_{MESF}^{(2)}, \ldots, I_{MESF}^{(n)}\} \to \mathbb{R}$$

$$I_{MESF} \mapsto \mu(I_{MESF})\exp((\sigma(I_{MESF}))^2 - 1)^{\frac{1}{2}}$$

wherein $I_{MESF}^{(n)}$ are the known values of fluorescence intensity for each set of the standardized beads, $\sigma(I_{MESF})$ is a standard deviation of a natural logarithm of bead intensities measured in the instrument, and $\mu(IMESF)$ is the mean intensity.

4. The method of claim 3, further comprising:
  modifying the dissimilarity matrix by a weighting function that includes large values for fluorescence intensities that are easy to distinguish and low values for fluorescence intensities that are difficult to distinguish, thereby scaling the dissimilarity matrix to include measurement precision.

5. The method of claim 4, wherein the weighting function comprises $$w = 1 \bigg/ \left(1 + \sqrt{\frac{\sigma_i^2}{I_i^2} + \frac{\sigma_j^2}{I_j^2}}\right).$$

6. The method of claim 1, wherein the bin numbers i and j are substituted by fluorescence intensity values (I) obtained from a smoothed curve representing a relation between flow cytometry histogram bin number and absolute intensity, such that $$A_j^i = \exp\left(\gamma \frac{I_{ij}}{I_{max}}\right)^\delta,$$

where $$I_{i,j} = |I_i - I_j|, \; I_{max} = \max_{i,j}\{I_{ij}\}.$$

7. The method of claim 1, wherein constructing the statistical test comprises:
  running a plurality of biological control samples of a proposed experiment through the instrument to produce a plurality of histograms corresponding thereto;
  randomly sampling, with replacement and a plurality of times, the plurality of histograms of the biological control samples to produce additional histograms for the set of histograms;
  applying the metric to calculate a set of distances between the set of histograms, expressed in fluorescence intensity values, whereby the distribution of distances demonstrate effects of instrumental variability as well as biological and biochemical variability of labeling procedures of the experiment; and
  assigning statistical levels of significance to the distance values measured between histograms of biological samples.

8. The method of claim 7, wherein the random sampling and applying the metric steps comprise generating bootstrapped histograms and creating distributions of the distances between the set of bootstrapped histograms, wherein the assigning statistical levels comprises:
  calculating a percentile of distribution of distances between bootstrapped histograms of the control sample; and
  determining that the measured test sample is statistically different than the control samples if the distance between the test and the control fall into a predetermined interval of percentiles of the distribution of bootstrapped distances of the control samples.

9. The method of claim 8, wherein the predetermined interval comprises a first ($1^{st}$) percentile, wherein the distance for the control sample is greater than the distance for the test samples in less than 1% of a total number of the bootstrapped calculations performed the plurality of times.

10. The method of claim 1, further comprising:
  storing the dissimilarity matrix in relation to measurement metadata in a database coupled with the computer; and
  comparing a plurality of dissimilarity matrices generated in different experiments on different days to detect a change in quality of measured fluorescence intensity values of the instrument.

11. A system for quantifying and validating differences between measured values of fluorescence intensities using a flow cytometer or other fluorescence-based instrument, the system comprising:
  a) a flow cytometer through which to run multiple sets of standardized particles to generate at least one calibration histogram for each set of particles, the histograms containing fluorescence intensity values;
  b) a computer coupled with the flow cytometer to calibrate a distance function configured to measure distances between the calibration histograms generated by the sets of standardized particles, the computer having a memory and a processor configured to:
    i) construct a quadratic form (QF) metric using the distance function, where the QF metric comprises $$QF(h,f) = (h-f)^T A_j^i (h-f) = \sum_{i=a}^{n}\sum_{j=1}^{n} a_{ij}(h_i - f_i)(h_j - f_j),$$

where h and f are histograms, and A comprises a bin-to-bin dissimilarity matrix that is an n×n positive semi-definite matrix, n being the number of bins in histograms h and f; and
    ii) populate entries of the dissimilarity matrix with elements using parameters that control at least groups of the elements such that the metric maximizes the following conditions at substantially the whole range of fluorescence intensity values for the sets of standardized particles: (A) the distance function of two histograms representing two sets of different standardized particles substantially equals the difference of their fluorescence intensity values or the logarithms of their fluorescence intensity values; and (B) the distance function of two histograms representing fluorescence of two sets of identical particles is substantially zero; wherein each set of particles is characterized by a fluorescence intensity corresponding to a known number of fluorochromes of interest, wherein the dissimilarity matrix further includes distances between bins i,j of histograms h,j which list counts of detected fluorescence intensities corresponding to each of the cytometry histogram bins;
    iii) compute $$A_j^i = \exp\left(\gamma \frac{d_{ij}}{d_{max}}\right)^\delta,$$

where $$d_{i,j} = |i - j|, \; d_{max} = \max_{i,j}\{d_{i,j}\};$$

and
    iv) iteratively determine γ and δ of $A_j^i$ to control a global shape of the dissimilarity matrix such that maximizes the conditions of b)ii)A) and b)ii)B);

c) wherein the processor is further configured to:
  i) apply the constructed metric to a set of flow cytometry histograms generated by the instrument for a plurality of biological samples, to determine distances between the histograms;
  ii) construct and apply a statistical test using the constructed metric to determine a statistical significance of the distances between the histograms; and
  iii) determine whether the histogram results from the biological samples are reliable based on the statistical significance.

12. The system of claim 11, wherein the computer comprises a server coupled with the flow cytometer over a network.

13. The system of claim 12, wherein the server is configured to:
  compare the dissimilarity matrix with previously-stored dissimilarity matrices generated in previous calibration experiments for the same set of standardized particles; and
  communicate a warning to an operator of the flow cytometer if the dissimilarity matrix is significantly different from the previously-stored dissimilarity matrices, indicating instability of the instrument.

14. The system of claim 11, wherein the processor is further configured to normalize the histograms h and f so that $0 \leq \{f, h\} \leq 1$ and $\Sigma_i h_i = \Sigma_i f_i = 1$.

15. The system of claim 11, wherein the standardized particles comprise standardized beads, wherein the fluorescence intensity is expressed in molecules of equivalent soluble fluorophore (MESF), and wherein the processor is further configured to initially estimate $\gamma$ and $\delta$ by approximating the shape of the dissimilarity matrix by a function fitted to the following relation:

$$f: \{I_{MESF}^{(1)}, I_{MESF}^{(2)}, \ldots, I_{MESF}^{(n)}\} \to \mathbb{R}$$

$$I_{MESF} \mapsto \mu(I_{MESF}) \exp((\sigma(I_{MESF}))^2 - 1)^{\frac{1}{2}}$$

wherein $I_{MESF}^{(n)}$ are the known values of fluorescence intensity for each set of the standardized beads, $\sigma(I_{MESF})$ is a standard deviation of a natural logarithm of bead intensities measured in the instrument, and $\mu(I_{MESF})$ is the mean intensity.

16. The system of claim 11, wherein i and j are substituted by fluorescence intensity values (I) obtained from a smoothed curve representing a relation between flow cytometry histogram bin number and absolute intensity, such that $$A_j^i = \exp\left(\gamma \frac{I_{ij}}{I_{max}}\right)^{\delta},$$

where $$I_{i,j} = |I_i - I_j|, I_{max} = \max_{i,j}\{I_{ij}\}.$$

17. The system of claim 16, wherein the processor modifies the dissimilarity matrix by a weighting function that includes large values for fluorescence intensities that are easy to distinguish and low values for fluorescence intensities that are difficult to distinguish, thereby scaling the dissimilarity matrix to include measurement precision, wherein the weighting function comprises:

$$w = 1 \bigg/ \left(1 + \sqrt{\frac{\sigma_i^2}{I_i^2} + \frac{\sigma_j^2}{I_j^2}}\right).$$

18. The system of claim 11, wherein at least one biological control sample of a proposed experiment are run through the flow cytometer to produce a plurality of histograms corresponding thereto, wherein to construct the statistic test, the processor is further configured to:
  apply the metric to calculate a set of distances between the set of histograms of the at least one control sample, expressed as fluorescence intensity values, whereby the distribution of the distances demonstrate effects of instrumental variability as well as biological and biochemical variability of labeling procedures of the experiment; and
  assign statistical levels of significance to QF distance values measured between histograms of biological samples.

19. The system of claim 18, wherein the processor is further configured to randomly sample, with replacement and a plurality of times, the plurality of histograms of the at least one biological control sample to produce additional histograms for the set of histograms before the set of distances therebetween are calculated.

20. The system of claim 18, wherein the cytometer measures fluorescence intensities in MESF of the biological test sample corresponding to the at least one control sample to generate a set of histograms for the test sample, wherein the processor is further configured to:
  calculate empirical critical values for the a least one control sample, each critical value being determined by:
    generating confidence intervals by bootstrapping the histograms of the control samples; and
    setting each critical value as being within a desired percentile of a corresponding confidence interval of a control sample.

21. The system of claim 20, wherein the critical values are calculated from histogram results of the standardized particles.

22. The system of claim 20, wherein the computer is further configured to communicate with a repair company to set up a repair call for the flow cytometer in response to the difference between a current dissimilarity matrix and the set of dissimilarity matrices generated previously falling outside the critical value.

23. The system of claim 11, further comprising:
  a database in which to store the dissimilarity matrix;
  wherein the processor is further configured to:
    store the dissimilarity matrix in relation to measurement metadata in the database; and
    compare a plurality of dissimilarity matrices generated in different experiments to detect a change in reliability of measured fluorescence intensity values of the flow cytometer.

24. A non-transitory computer-readable medium comprising instructions for quantifying and validating differences between measured values of fluorescence intensities using a flow cytometer, the instructions executable by a computer having a memory and processor coupled with the flow cytometer, the computer-readable medium comprising:
  instructions to direct the processor to receive at least one calibration histogram for each set of standardized particles run through the flow cytometer, the histograms containing fluorescence intensity values;

instructions to direct the processor to calibrate a distance function configured to measure distances between the calibration histograms generated by the sets of standardized particles, to direct the processor to:
i) construct a quadratic form (QF) metric using the distance function, where the QF metric comprises $$QF(h, f) = (h - f)^T A^i_j (h - f) = \sum_{i=a}^{n} \sum_{j=1}^{n} a_{ij}(h_i - f_i)(h_j - f_j),$$

where h and f are histograms, and A comprises a bin-to-bin dissimilarity matrix that is an n×n positive semi-definite matrix, n being the number of bins in histograms h and f; and
ii) populate entries of the dissimilarity matrix with elements using parameters that control at least groups of the elements such that the metric maximizes the following conditions at substantially the whole range of fluorescence intensity values for the sets of standardized particles: (A) the distance function of two histograms representing two sets of different standardized particles substantially equals the difference of their fluorescence intensity values or the logarithms of their fluorescence intensity values; and (B) the distance function of two histograms representing fluorescence of two sets of identical particles is substantially zero; wherein each set of particles is characterized by a fluorescence intensity corresponding to a known number of fluorochromes of interest, wherein the dissimilarity matrix further includes distances between bins i,j of histograms h,j which list counts of detected fluorescence intensities corresponding to each of the cytometry histogram bins;
iii) compute $$A^i_j = \exp\left(\gamma \frac{d_{ij}}{d_{max}}\right)^\delta,$$

where $$d_{i,j} = |i - j|, d_{max} = \max_{i,j}\{d_{i,j}\};$$

and
iv) iteratively determine $\gamma$ and $\delta$ of $A_j^i$ to control a global shape of the dissimilarity matrix such that maximizes the conditions of ii)A) and ii)B);
instructions to direct the processor to apply the constructed metric to a set of flow cytometry histograms generated by the flow cytometer for a plurality of biological samples, to determine distances between the histograms;
instructions to direct the processor to construct and apply a statistical test using the constructed metric to determine a statistical significance of the distances between the histograms; and
instructions to determine whether the histogram results from the biological samples are reliable based on the statistical significance.

* * * * *